(12) United States Patent
Schwab et al.

(10) Patent No.: US 6,580,009 B2
(45) Date of Patent: Jun. 17, 2003

(54) FLEXIBLE PREPARATION OF PROPENE AND HEXENE

(75) Inventors: Peter Schwab, Bad Dürkheim (DE); Ralf Schulz, Speyer (DE); Sylvia Huber, Zwingenberg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 188 days.

(21) Appl. No.: 09/803,147

(22) Filed: Mar. 12, 2001

(65) Prior Publication Data

US 2002/0002317 A1 Jan. 3, 2002

(30) Foreign Application Priority Data

Mar. 17, 2000 (DE) .......................................... 100 13 253

(51) Int. Cl.$^7$ ............................... C07C 6/04; C07C 6/02
(52) U.S. Cl. ....................... 585/324; 585/643; 585/646; 585/647
(58) Field of Search ................................ 585/324, 643, 585/646, 647

(56) References Cited

U.S. PATENT DOCUMENTS 5,057,638 A   10/1991   Sweeney ..................... 585/324

FOREIGN PATENT DOCUMENTS

| DE | 198 13 720 | 2/1999 |
|---|---|---|
| DE | 199 32 060 | 1/2001 |
| EP | 0 742 195 | 11/1996 |

*Primary Examiner*—Thuan D. Dang
(74) *Attorney, Agent, or Firm*—Keil & Weinkauf

(57) ABSTRACT

The process for preparing propene and hexene from a raffinate II feed stream comprising olefinic $C_4$-hydrocarbons comprises a) a metathesis reaction in which butenes present in the feed stream are reacted with ethene in the presence of a metathesis catalyst comprising at least one compound of a metal of transition groups VIb, VIIb or VIII of the Periodic Table of the Elements to give a mixture comprising ethene, propene, butenes, 2-pentene, 3-hexene and butanes, using, based on the butenes, from 0.05 to 0.6 molar equivalents of ethene, b) firstly fractionally distilling the product stream obtained in this way to give a low-boiling fraction A comprising $C_2$–$C_3$-olefins and a high-boiling fraction comprising $C_4$–$C_6$-olefins and butanes, c) subsequently fractionally distilling the low-boiling fraction A obtained from b) to give an ethene-containing fraction and a propene-containing fraction, with the ethene-containing fraction being returned to the process step a) and the propene-containing fraction being discharged as product, d) subsequently fractionally distilling the high-boiling fraction obtained from b) to give a low-boiling fraction B comprising butenes and butanes, a pentene-containing intermediate-boiling fraction C and a hexene-containing high-boiling fraction D, e) where the fractions B and C are completely or partly returned to the process step a) and the fraction D is discharged as product.

11 Claims, 2 Drawing Sheets

FLEXIBLE PREPARATION OF PROPENE AND HEXENE

Figure 1:
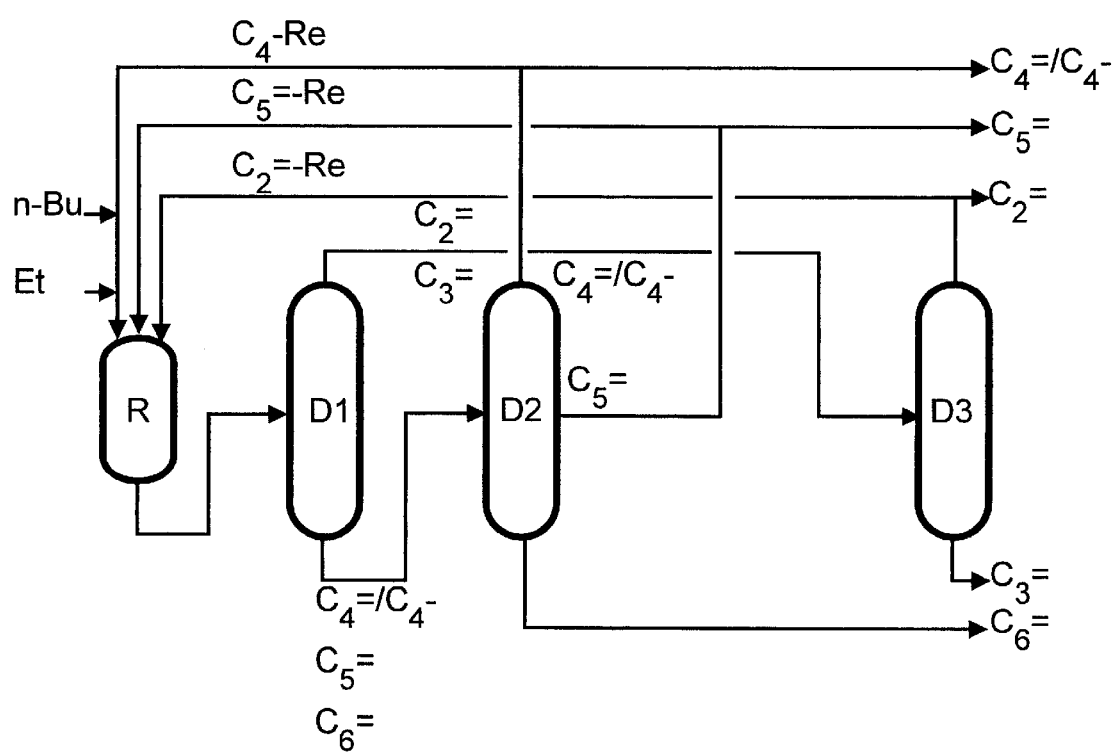

The present invention relates to a process for converting olefinic $C_4$-hydrocarbons, for example from steam crackers or FCC plants, into propene and hexene by means of a metathesis reaction.

Steam crackers represent the main source of basic petrochemicals such as ethene, propene, $C_4$-olefins and higher hydrocarbons. In the cracking process, it is necessary to transfer large quantities of energy at high temperatures in a short time span which is sufficient to carry out cracking but does not permit further reaction of the cracking products. In the cracking of hydrocarbons, the yield of ethene and propene is therefore determined essentially by the type of hydrocarbons used (naphtha, ethane, LPG, gas oil, or the like)
the cracking temperature,
the residence time
and the partial pressures of the respective hydrocarbons.

The highest yield of ethene and propene is achieved at cracking temperatures in the range from 800 to 850° C. and residence times of from 0.2 to 0.5 s. The main product in this range is always ethene, with the $C_3/C_2$ product ratio of from about 0.5 to 0.7 being able to be increased slightly by varying the cracking conditions. The worldwide demand for propene is increasing more rapidly than that for ethene. This has the consequence, inter alia, that processes for downstream utilization of the higher hydrocarbons formed in the cracking process, e.g. $C_4$, with a view to optimizing the propene yield are becoming increasingly important. A suitable process is olefin metathesis.

Olefin metathesis (disproportionation) is, in its simplest form, the reversible, metal-catalyzed transalkylidenation of olefins by rupture and reformation of C=C double bonds according to the following equation:

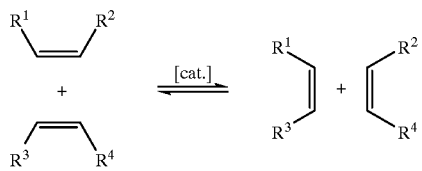

In the specific case of the metathesis of acyclic olefins, a distinction is made between self-metathesis in which an olefin is transformed into a mixture of two olefins having differing molar masses (for example: propene→ethene+2-butene) and cross-metathesis or cometathesis which is a reaction of two different olefins (propene+1-butene→ethene+2-pentene). If one of the reactants is ethene, this is generally referred to as an ethenolysis.

Suitable metathesis catalysts are, in principle, homogeneous and heterogeneous transition metal compounds, in particular those of elements of transition groups VI to VIII of the Periodic Table of the Elements, and also homogeneous and heterogeneous catalyst systems in which these compounds are present.

Different metathesis processes starting from $C_4$ streams have been described.

U.S. Pat. No. 5,057,638 relates to a process for preparing 1-hexene, comprising the process steps:
a) metathesis of 1-butene to give a mixture of 3-hexene and ethene,
b) separation of the 3-hexene from the product mixture obtained in step a),
c) reaction of the 3-hexene with an electrophile containing reactive hydrogen, preferably derived from water or carboxylic acid, under acid conditions which allow the addition of the electrophilic component to the C=C bond (e.g. hydration),
d) cracking of the product from step c), e.g. by dehydration, to produce a mixture of n-hexenes in which 1-hexene is present in economically acceptable amounts.

EP-A-0 742 195 relates to a process for converting $C_4$ or $C_5$ fractions into ethers and propylene. In the process starting from $C_4$ fractions, diolefins and acetylenic impurities present are firstly selectively hydrogenated, with the hydrogenation being associated with an isomerization of 1-butene to 2-butene. The yield of 2-butenes is said to be maximized in this way. The ratio of 2-butene to 1-butene after the hydrogenation is about 9:1. This is followed by etherification of the resulting isoolefins, with the ethers being separated from the $C_4$ fraction. Oxygen-containing impurities are then separated off. The resulting product, which comprises predominantly 2-butene in addition to alkanes, is then reacted with ethylene in the presence of a metathesis catalyst in order to obtain a reaction product comprising propylene as product. The metathesis is carried out in the presence of a catalyst comprising rhenium oxide on a support.

DE-A-198 13 720 relates to a process for preparing propene from a $C_4$ stream. Here, butadiene and isobutene are firstly removed from the $C_4$ stream. Oxygen-containing impurities are then separated off and a two-stage metathesis of the butenes is carried out. Firstly, 1-butene and 2-butene are converted into propylene and 2-pentene. The 2-pentene obtained is then reacted further with added ethylene to form propylene and 1-butene.

DE-A-199 32 060, which has earlier priority but is not a prior publication, relates to a process for preparing $C_5$-/$C_6$-olefins by reaction of a feed stream comprising 1-butene, 2-butene and isobutene to give a mixture of $C_{2-6}$ olefins. In this process, propene, in particular, is obtained from butenes. In addition, hexene and methylpentene are discharged as product. No ethene is added in the metathesis. If desired, ethene formed in the metathesis is returned to the reactor.

The world market prices of ethene and propene are subject to change. In addition, there is a demand for pentene and hexene olefin fractions which can be used as inexpensive alternative raw materials for plasticizer alcohols or surfactant alcohols. To be able to react to the price changes on the world market, there is a need for a process for the flexible preparation of propene and hexene which allows the product spectrum obtained to be appropriately matched to the price difference between ethene and propene. For example, it should be possible to obtain pentene and hexene olefin fractions and also propene flexibly using smaller to larger amounts of ethene.

It is an object of the present invention to provide a flexibly controllable catalytic process for obtaining propene and hexene from inexpensive olefin-containing $C_4$-hydrocarbon mixtures. It should be possible to make a very flexible ethene addition by means of which the relative amounts of products obtained, in particular propene and hexene, can be influenced. In this way, the addition of value to steam cracker by-products should be improved, with the products having the greatest added value being able to be obtained.

We have found that this object is achieved by a process for preparing propene and hexene from a raffinate II feed stream comprising olefinic $C_4$-hydrocarbons, which comprises
a) a metathesis reaction in which butenes present in the feed stream are reacted with ethene in the presence of a metathesis catalyst comprising at least one compound of a metal of transition groups VIb, VIIb or VIII of the Periodic Table of the Elements to give a mixture comprising ethene, propene, butenes, 2-pentene, 3-hexene and butanes, using, based on the butenes, from 0.05 to 0.6 molar equivalents of ethene, b) firstly fractionally distilling the product stream obtained in this way to give a low-boiling fraction A comprising $C_2$–$C_3$-olefins and a high-boiling fraction comprising $C_4$–$C_6$-olefins and butanes, c) subsequently fractionally distilling the low-boiling fraction A obtained from b) to give an ethene-containing fraction and a propene-containing fraction, with the ethene-containing fraction being returned to the process step a) and the propene-containing fraction being discharged as product, d) subsequently fractionally distilling the high-boiling fraction obtained from b) to give a low-boiling fraction B comprising butenes and butanes, a pentene-containing intermediate-boiling fraction C and a hexene-containing high-boiling fraction D, e) where the fractions B and C are completely or partly returned to the process step a) and the fraction D is discharged as product.

The individual streams and fractions can comprise or consist of the compounds mentioned. In the case of their consisting of the streams or compounds, the presence of relatively small amounts of other hydrocarbons is not ruled out.

In this process, in a single-stage reaction procedure, a fraction comprising $C_4$-olefins, preferably n-butenes and butanes, is reacted in a metathesis reaction with variable amounts of ethene over a homogeneous or preferably heterogeneous metathesis catalyst to give a product mixture of (inert) butanes, unreacted 1-butene, 2-butene and the metathesis products ethene, propene, 2-pentene and 3-hexene. The desired products propene and 3-hexene are discharged and the remaining products and unreacted compounds are completely or partly recirculated to the metathesis. They are preferably recirculated essentially completely, with only small amounts being discharged to avoid accumulation. Ideally, there is no accumulation and all compounds apart from 3-hexene and propene are returned to the metathesis.

According to the present invention, from 0.05 to 0.6, preferably from 0.1 to 0.5, molar equivalents of ethene are used, based on the butenes in the $C_4$ feed stream. Thus, only small amounts of ethene compared to the prior art are used. For example, EP-A-0 742 195 uses at least equivalent molar amounts of ethene, based on the butenes. Preference is given to employing an excess of ethene.

If no addition of ethene were to be introduced, only about 1.5% at most, based on the reaction products, of ethene would be formed in the process. This ethene is recirculated. In contrast to DE-A-199 32 060, which has earlier priority but is not a prior publication, relatively large amounts of ethene are used according to the present invention, with the amounts used being significantly lower than in the known processes for preparing propene.

In addition, the maximum possible amounts of $C_4$ products and $C_5$ products present in the reactor output are recirculated according to the present invention. This applies particularly to the recirculation of unreacted 1-butene and 2-butene and of 2-pentene formed.

If small amounts of isobutene are still present in the $C_4$ feed stream, small amounts of branched hydrocarbons can also be formed.

The amount of branched $C_5$- and $C_6$-hydrocarbons which may be additionally formed in the metathesis product is dependent on the isobutene content of the $C_4$ feed and is preferably kept as small as possible (<3%).

To describe the process of the present invention in more detail in a plurality of variations, the reaction taking place in the metathesis reactor will be subdivided into three important individual reactions:

1. Cross-metathesis of 1-buten with 2-butene

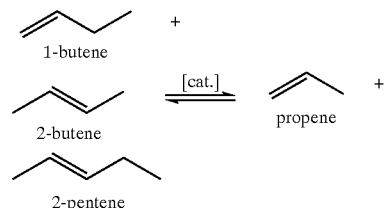

2. Self-metathesis of 1-butene

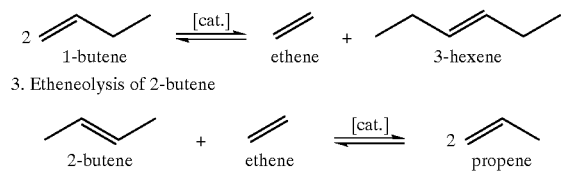

3. Etheneolysis of 2-butene

Depending on the respective demand for the target products propene and 3-hexene (the term 3-hexene encompasses any isomers formed), the external mass balance of the process can be influenced in a targeted way by means of variable use of ethene and by shifting the equilibrium by recirculation of certain substreams. Thus, for example, the yield of 3-hexene is increased by the cross-metathesis of 1-butene with 2-butene being suppressed by recirculation of 2-pentene to the metathesis step, so that no or very little 1-butene is consumed here. The self-metathesis of 1-butene to give 3-hexene which then proceeds preferentially additionally forms ethene which reacts in a subsequent reaction with 2-butene to give the desired product propene.

Olefin mixtures comprising 1-butene and 2-butene and possibly isobutene are obtained, inter alia, as $C_4$ fraction in various cracking processes such as steam cracking or fluid catalytic cracking. As an alternative, it is possible to use butene mixtures as are obtained in the dehydrogenation of butanes or by dimerization of ethene. Butanes present in the $C_4$ fraction behave as inerts. Dienes, alkynes or enynes are removed using customary methods such as extraction or selective hydrogenation prior to the metathesis step of the present invention.

The butene content of the $C_4$ fraction used in the process is from 1 to 100% by weight, preferably from 60 to 90% by weight. Here, the butene content is based on 1-butene, 2-butene and isobutene.

Preference is given to using a $C_4$ fraction obtained in steam cracking or fluid catalytic cracking or in the dehydrogenation of butane.

Raffinate II is preferably used as $C_4$ fraction, with the $C_4$ stream being freed of interfering impurities by appropriate treatment over adsorbent guard bets, preferably over high surface area aluminum oxides or molecular sieves, prior to the metathesis reaction.

The low-boiling fraction A obtained from step b) and comprising $C_2$–$C_3$-olefins is fractionally distilled to give an ethene-containing fraction and a propene-containing fraction. The ethene-containing fraction is then returned to process step a), i.e. the metathesis, and the propene-containing fraction is discharged as product.

In step d), the separation into low-boiling fraction B, intermediate-boiling fraction C and high-boiling fraction D can be carried out, for example, in a dividing wall column. Here, the low-boiling fraction B is obtained at the top, the intermediate-boiling fraction C is obtained at a middle outlet and the high-boiling fraction D is obtained as bottoms.

However, to be able to handle the different amounts of products obtained in the flexibly controlled process more readily, it is advantageous to carry out a two-stage fractionation of the high-boiling fraction obtained from b). The high-boiling fraction obtained from b) is preferably firstly fractionally distilled to give a low-boiling fraction B comprising butenes and butanes and a high-boiling fraction comprising 2-pentene and 3-hexene. The high-boiling fraction is then fractionally to distilled to give the fractions C and D. The two embodiments are explained in more detail in FIGS. 1 and 2.

The metathesis reaction is preferably carried out in the presence of heterogeneous metathesis catalysts which are not or only slightly isomerization-active and are selected from the group consisting of transition metal compounds of metals of groups VIb, VIIb or VIII of the Periodic Table of the Elements applied to inorganic supports.

The preferred metathesis catalyst is rhenium oxide on a support, preferably on γ-aluminum oxide or on $Al_2O_3/B_2O_3/SiO_2$ mixed supports.

In particular, $Re_2O_7/\gamma-Al_2O_3$ having a rhenium oxide content of from 1 to 20%, preferably from 3 to 15%, particularly preferably from 6 to 12% (% by weight), is used as catalyst.

The metathesis is, when carried out in a liquid phase, preferably carried out at from 0 to 150° C., particularly preferably from 20 to 80° C., and a pressure of from 2 to 200 bar, particularly preferably from 5 to 30 bar.

If the metathesis is carried out in the gas phase, the temperature is preferably from 20 to 300° C., particularly preferably from 50 to 200° C. In this case, the pressure is preferably from 1 to 20 bar, particularly preferably from 1 to 5 bar.

In the context of work on improving the value added to steam cracker by-products, an additional object is to develop a flexibly controlled process sequence for utilization of $C_4$ fractions. The aim is to convert $C_4$-olefins into higher-priced olefin fractions, thus adding value. As feed stock, crude $C_4$ fraction from steam crackers or FCC plants is available.

This object is achieved according to the present invention by a process for preparing $C_5/C_6$-olefins and propene from steam cracker or refinery $C_4$ streams, which comprises the substeps (1) removal of butadiene and acetylenic compounds by, if appropriate, extraction of butadiene with a butadiene-selective solvent and subsequent/or selective hydrogenation of butadienes and acetylenic compounds present in crude $C_4$ fraction to give a reaction product comprising n-butenes and isobutene and essentially no butadienes and acetylenic compounds, (2) removal of isobutene by reaction of the reaction product obtained in the preceding step with an alcohol in the presence of an acid catalyst to form an ether, removal of the ether and the alcohol, which can be carried out simultaneously with or after the etherification, to give a reaction product comprising n-butenes and possibly oxygen-containing impurities, with the ether formed being able to be discharged or redissociated to obtain pure isobutene and the etherification step being able to be followed by a distillation step for removing isobutene, where, if desired, introduced $C_3$-, i-$C_4$- and $C_5$-hydrocarbons can also be separated off by distillation during the work-up of the ether, or oligomerization or polymerization of isobutene from the reaction product obtained in the preceding step in the presence of an acid catalyst whose acid strength is suitable for the selective removal of isobutene as oligoisobutene or polyisobutene, to give a stream containing from 0 to 15% of residual isobutene, (3) removal of the oxygen-containing impurities from the output from the preceding steps over appropriately selected adsorber materials, (4) metathesis reaction of the resulting raffinate II stream as described.

The substep of selective hydrogenation of butadiene and acetylenic impurities present in crude $C_4$ fraction is preferably carried out in two stages by bringing the crude $C_4$ fraction in the liquid phase into contact with a catalyst comprising at least one metal selected from the group consisting of nickel, palladium and platinum on a support, preferably palladium on aluminum oxide, at from 20 to 200° C., a pressure of from 1 to 50 bar, a volume flow of from 0.5 to 30 $m^3$ of fresh feed per $m^3$ of catalyst per hour and a ratio of recycle to fresh feed of from 0 to 30 with a molar ratio of hydrogen to diolefins of from 0.5 to 50, to give a reaction product in which, apart from isobutene, the n-butenes 1-butene and 2-butene are present in a molar ratio of from 2:1 to 1:10, preferably from 2:1 to 1:3, and in which essentially no diolefins and acetylenic compounds are present. For a maximum yield of hexene, 1-butene is preferably present in excess, while for a high propene yield, 2-butene is preferably present in excess. This means that the overall molar ratio in the first case can be from 2:1 to 1:1 and in the second case can be from 1:1 to 1:3.

The substep of butadiene extraction from crude $C_4$ fraction is preferably carried out using a butadiene-selective solvent selected from the group consisting of polar aprotic solvents such as acetone, furfural, acetonitrile, dimethylacetamide, dimethylformamide and N-methylpyrrolidone to give a reaction product in which, after subsequent selective hydrogenation/isomerization, the n-butenes 1-butene and 2-butene are present in a molar ratio of from 2:1 to 1:10, preferably from 2:1 to 1:3.

The substep of isobutene etherification is preferably carried out in a three-stage reactor cascade using methanol or isobutanol, preferably isobutanol, in the presence of an acid ion exchanger, in which the stream to be etherified flows through fixed-bed catalysts from the top downward, where the reactor inlet temperature is from 0 to 60° C., preferably from 10 to 50° C., the outlet temperature is from 25 to 85° C., preferably from 35 to 75° C., the pressure is from 2 to 50 bar, preferably from 3 to 20 bar, and the ratio of isobutanol to isobutene is from 0.8 to 2.0, preferably from 1.0 to 1.5, and the total conversion corresponds to the equilibrium conversion.

The substep of isobutene removal is preferably carried out by oligomerization or polymerization of isobutene in the presence of a catalyst selected from the group consisting of homogeneous and heterogeneous Brönsted and Lewis acids, starting from the reaction product obtained after the above-described stages of butadiene extraction and/or selective hydrogenation.

Selective Hydrogenation of Crude $C_4$ Fraction

Alkynes, alkynenes and alkadienes are undesirable substances in many industrial syntheses owing to their tendency to polymerize or their pronounced tendency to form complexes with transition metals. Thus, they sometimes have a very strong adverse effect on the catalysts used in these reactions.

The $C_4$ stream from a steam cracker contains a high proportion of multiply unsaturated compounds such as 1,3- butadiene, 1-butyne (ethylacetylene) and butenyne (vinylacetylene). Depending on downstream processing, the multiply unsaturated compounds are either extracted (butadiene extraction) or selectively hydrogenated. In the former case, the residual content of multiply unsaturated compounds is typically from 0.05 to 0.3% by weight, while in the latter case it is typically from 0.1 to 4.0% by weight. Since the residual amounts of multiply unsaturated compounds likewise interfere in further processing, a further reduction in concentration to <10 ppm by selective hydrogenation is necessary. In order to obtain the highest possible proportion of the desired butenes, overhydrogenation to butanes needs to be kept as low as possible.

Suitable hydrogenation catalysts which have been described are:

J. P. Boitiaux, J. Cosyns, M. Derrien and G. Lèger, Hydrocarbon Processing, March 1985, p.51–59

Description of bimetallic catalysts for selective hydrogenations of $C_2$-, $C_3$-, $C_4$-, $C_5$- and $C_{5+}$-hydrocarbon streams. Bimetallic catalysts comprising group VIII and Group IB metals, in particular, display improvements in selectivity compared to supported, pure Pd catalysts.

DE-A-2 059 978

Selective hydrogenation of unsaturated hydrocarbons in a liquid phase over a Pd/alumina catalyst. To prepare the catalyst, the alumina support having a BET surface area of 120 m$^2$/g is firstly subjected to steam treatment at 110–300° C. and subsequently calcined at 500–1200° C. Finally, the Pd compound is applied and the catalyst is calcined at 300–600° C.

EP-A-0 564 328 and EP-A-0 564 329

Catalyst comprising, inter alia, Pd and In or Ga on supports. The catalyst combination makes it possible to be used without addition of CO at high activity and selectivity.

EP-A-0 089 252

Supported Pd, Au Catalysts.

The preparation of the catalysts comprises the following steps:

impregnation of a mineral support with a Pd compound calcination under $O_2$-containing gas treatment with a reducing agent impregnation with a halogenated Au compound treatment with a reducing agent washing out of the halogen by means of a basic compound calcination under $O_2$-containing gas.

U.S. Pat. No. 5,475,173

Catalyst comprising Pd and Ag and alkali metal fluoride on an inorganic support.

Advantages of the catalyst: KF addition results in increased butadiene conversion and better selectivity to butenes (i.e. reduced overhydrogenation to n-butane).

EP-A-0 653 243

The active component of this catalyst is present predominantly in the mesopores and macropores. In addition, the catalyst has a large pore volume and a low tapped density. Thus, the catalyst from Example 1 has a tapped density of 383 g/l and a pore volume of 1.17 ml/g.

EP-A-0 211 381

Catalyst comprising group VIII metal (preferably Pt) and at least one metal selected from the group consisting of Pb, Sn and Zn on an inorganic support. The preferred catalyst consists of Pt/ZnAl$_2$O$_4$. The specified promoters Pb, Sn and Zn improve the selectivity of the Pt catalyst.

EP-A-0 722 776

Catalyst comprising Pd and at least one alkali metal fluoride and optionally Ag on inorganic supports (Al$_2$O$_3$, TiO$_2$ and/or ZrO$_2$). The catalyst combination makes a selective hydrogenation in the presence of sulfur compounds possible.

EP-A-0 576 828

Catalyst based on noble metal and/or noble metal oxide on Al$_2$O$_3$ supports having a defined X-ray diffraction pattern. The support comprises n-Al$_2$O$_3$ and/or γ-Al$_2$O$_3$. Owing to the specific support, the catalyst has high initial selectivity and can therefore be used immediately for the selective hydrogenation of unsaturated compounds.

JP 01110594

Supported Pd Catalyst

A further electron donor is additionally used. This consists either of a metal deposited on the catalyst, for example Na, K, Ag, Cu, Ga, In, Cr, Mo or La, or an addition to the hydrocarbon feed stock, for example alcohol, ether or N-containing compounds. The measures described can achieve a reduction in the 1-butene isomerization.

DE-A-31 19 850

Catalyst comprising an SiO$_2$ or Al$_2$O$_3$ support having a surface area of 10–200 m$^2$/g or $\leq$100 m$^2$/g with Pd and Ag as active component. The catalyst is used primarily for the hydrogenation of low-butadiene hydrocarbon streams.

EP-A-0 780 155

Catalyst comprising Pd and a group IB metal on an Al$_2$O$_3$ support, in which at least 80% of the Pd and 80% of the group IB metal are present in an outer shell between $r_1$ (=radius of the pellet) and 0.8-$r_1$.

Alternative: Extraction of Butadiene from Crude $C_4$ Fraction

The preferred method of isolating butadiene is based on the physical principle of extractive distillation. Addition of selective organic solvents lowers the volatility of specific components of a mixture, in this case butadiene. For this reason, they remain together with the solvent in the bottoms from the distillation column while the accompanying substances which were previously not able to be separated off by distillation can be taken off at the top. Solvents employed for the extractive distillation are mainly acetone, furfural, acetonitrile, dimethylacetamide, dimethylformamide (DMF) and N-methylpyrrolidone (NMP). Extractive distillations are particularly useful for butadiene-rich $C_4$ cracker fractions having a relatively high proportion of alkynes, for example methylacetylene, ethylacetylene and vinylacetylene, and also methylallene.

The simplified principle of a solvent extraction from crude $C_4$ fraction can be described as follows: The completely vaporized $C_4$ fraction is fed into an extraction column at its lower end. The solvent (DMF, NMP) flows from the top in the opposite direction to the gas mixture and on its way downward becomes laden with the more soluble butadiene and small amounts of butenes. At the lower end of the extraction column, part of the pure butadiene which has been isolated is fed in in order to strip out most of the butenes. The butenes leave the separation column at the top. In a further column, referred to as degaser, the butadiene is separated from the solvent by boiling out and is subsequently subjected to final distillation.

The reaction product from an extractive butadiene distillation is usually fed to the second stage of a selective hydrogenation in order to reduce the residual butadiene content to <10 ppm.

The $C_4$ stream remaining after butadiene has been separated off is referred to as $C_4$ raffinate or raffinate I and comprises mainly the components isobutene, 1-butene, 2-butenes and n-butane and isobutane.

Separation of Isobutene from Raffinate I

In the further fractionation of the $C_4$ stream, preference is given to isolating isobutene next, since it differs in its branching and its higher reactivity from the other $C_4$ components. Apart from the possibility of a shape-selective molecular sieve separation, by means of which isobutene can be isolated in a purity of 99% and n-butenes and butane can be further desorbed by means of a higher-boiling hydrocarbon, this is done first and foremost by distillation using a deisobutenizer by means of which isobutene together with 1-butene and isobutane are separated off at the top and 2-butenes and n-butane together with residual amounts of isobutene and 1-butene remain in the bottoms, or extractively by reaction of isobutene with alcohols over acid ion exchangers. Methanol ($\rightarrow$MTBE) or isobutanol (IBTBE) is preferably used for this purpose.

The preparation of MTBE from methanol and isobutene is carried out at from 30 to 100° C. and slight overpressure in the liquid phase over acid ion exchangers. It is either carried out in two reactors or in a two-stage shaft reactor so as to achieve almost complete isobutene conversion (>99%). The pressure-dependent azeotrope formation between methanol and MTBE requires a multistage pressure distillation to isolate pure MTBE or isolation of pure MTBE is achieved by relatively new technology using methanol adsorption on adsorber resins. All other components of the $C_4$ fraction remain unchanged. Since small proportions of diolefins and acetylenes can shorten the life of the ion exchanger due to polymer formation, preference is given to using bifunctional PD-containing ion exchangers over which only diolefins and acetylenes are hydrogenated in the presence of small amounts of hydrogen. The etherification of the isobutene remains uninfluenced by this.

MTBE is used first and foremost for increasing the octane number of gasoline. Alternatively, MTBE and IBTBE can be redissociated in the gas phase at from 150 to 300° C. over acidic oxides to give pure isobutene.

A further possible way of separating isobutene from raffinate I is the direct synthesis of oligobutene/polyisobutene. In this way, reaction over homogeneous and heterogeneous acid catalysts, e.g. tungsten trioxide on titanium dioxide, can give, at isobutene conversion of up to 95%, an output stream which contains a maximum of 5% of residual isobutene.

The Purification of the Raffinate II Stream over Adsorber Materials

To improve the operating life of the catalysts used for the subsequent metathesis step, the use of a guard bed for removing catalyst poisons, for example water, oxygen-containing compounds, sulfur or sulfur compounds or organic halides, is necessary, as described above.

Processes for adsorption and adsorptive purification are described, for example, in W. Kast, Adsorption aus der Gasphase, VCH, Weinheim (1988). The use of zeolitic adsorbents is described in D. W. Breck, Zeolite Molecular Sieves, Wiley, New York (1974).

The removal of, specifically, acetaldehyde from $C_3$–$C_{15}$-hydrocarbons in the liquid phase can be carried out as described in EP-A-0 582 901.

Selective Hydrogenation of Crude $C_4$ Fraction

Butadiene (1,2- and 1,3-butadiene) and alkynes or alkenynes present in the crude $C_4$ fraction from a steam cracker or a refinery are firstly hydrogenated selectively in a two-stage process. In one embodiment, the $C_4$ stream from a refinery can also be fed directly into the second step of the selective hydrogenation.

The first step of the hydrogenation is preferably carried out over a catalyst comprising from 0.1 to 0.5% by weight of palladium on aluminum oxide as support. The reaction is carried out in the gas/liquid phase over a fixed bed (downflow mode) with a liquid circuit. The hydrogenation is carried out at from 40 to 80° C. and a pressure of from 10 to 30 bar, a molar ratio of hydrogen to butadiene of from 10 to 50 and an LHSV of up to 15 m$^3$ of fresh feed per m$^3$ of catalyst per hour and a ratio of recycle to fresh feed of from 5 to 20.

The second step of the hydrogenation is preferably carried out over a catalyst comprising from 0.1 to 0.5% by weight of palladium on aluminum oxide as support. The reaction is carried out in the liquid/gas phase over a fixed bed (downflow mode) with a liquid circuit. The hydrogenation is carried out at from 50 to 90° C. and a pressure of from 10 to 30 bar, a molar ratio of hydrogen to butadiene of from 1.0 to 10 and an LHSV of from 5 to 20 m$^3$ of fresh feed per m$^3$ of catalyst per hour and a ratio of recycle to fresh feed of from 0 to 15.

The reaction product obtained in this way is referred to as raffinate I and comprises, in addition to isobutene, 1-butene and 2-butene in a molar ratio of from 2:1 to 1:10, preferably from 2:1 to 1:3.

Alternatively: Separation of Butadiene from Crude $C_4$ Fraction by Extraction

The extraction of butadiene from crude $C_4$ fraction is carried out by means of BASF technology using N-methylpyrrolidone.

In one embodiment of the invention, the product from the extraction is fed to the second step of the above-described selective hydrogenation in order to remove residual amounts of butadiene; in this selective hydrogenation step, the desired ratio of 1-butene to 2-butene is set.

Separation of Isobutene via Etherification with Alcohols

In the etherification stage, isobutene is reacted with alcohols, preferably with isobutanol, over an acid catalyst, preferably an acid ion exchanger, to form ethers, preferably isobutyl tert-butyl ether. In one embodiment of the invention, the reaction is carried out in a three-stage reactor cascade in which the reaction mixture flows from the top downward through flooded fixed-bed catalysts. In the first reactor, the inlet temperature is from 0 to 60° C., preferably from 10 to 50° C.; the outlet temperature is from 25 to 85° C., preferably from 35 to 75° C., and the pressure is from 2 to 50 bar, preferably from 3 to 20 bar. At a ratio of isobutanol to isobutene of from 0.8 to 2.0, preferably from 1.0 to 1.5, the conversion is from 70 to 90%.

In the second reactor, the inlet temperature is from 0 to 60° C., preferably from 10 to 50° C.: the outlet temperature is from 25 to 85° C., preferably from 35 to 75° C., and the pressure is from 2 to 50 bar, preferably from 3 to 20 bar. The total conversion over the two stages is increased to from 85 to 99%, preferably from 90 to 97%.

In the third and largest reactor, equilibrium conversion is achieved at equal inlet and outlet temperatures of from 0 to 60° C., preferably from 10 to 50° C. The etherification and separation of the ether formed is followed by ether cleavage: the endothermic reaction is carried out over acid catalysts, preferably over heterogeneous acid catalysts, for example phosphoric acid on an $SiO_2$ support, at an inlet temperature of from 150 to 300° C., preferably from 200 to 250° C., and an outlet temperature of from 100 to 250° C., preferably from 130 to 220° C.

When $C_4$ fraction from an FCC plant is used, it has to be expected that propane in amounts of about 1% by weight, isobutene in amounts of from about 30 to 40% by weight and $C_5$ hydrocarbons in amounts of from about 3 to 10% will be introduced, which can adversely affect the subsequent process sequence. The work-up of the ether accordingly provides the opportunity of separating off the components mentioned by distillation.

The reaction product obtained in this way, referred to as raffinate II, has a residual isobutene content of from 0.1 to 3% by weight.

If larger amounts of isobutene are present in the product, for example when $C_4$ fractions from FCC plants are used or when isobutene is separated off by acid-catalyzed polymerization to polyisobutene (partial conversion), the raffinate stream which remains can, according to an embodiment of the invention, be worked up by distillation prior to further processing.

Purification of the Raffinate II Stream over Adsorber Materials

The raffinate II stream obtained after the etherification/polymerization (or distillation) is purified over at least one guard bed comprising high surface area aluminum oxides, silica gels, aluminosilicates or molecular sieves. The guard bed serves to dry the $C_4$ stream and to remove substances which could act as catalyst poisons in the subsequent metathesis step. The preferred adsorber materials are Selexsorb CD and CDO and also 3 Å and NaX molecular sieves (13×). The purification is carried out in drying towers at temperatures and pressures which are chosen so that all components are present in the liquid phase. If desired, the purification step is used to preheat the feed for the subsequent metathesis step.

The raffinate II stream which remains is virtually free of water, oxygen-containing compounds, organic chlorides and sulfur compounds.

When the etherification step is carried out using methanol for preparing MTBE, the formation of dimethyl ether as secondary component may make it necessary to combine a plurality of purification steps or to connect them in series.

To maximize the yield of propene and 3-hexene, the process of the present invention is preferably carried out using the following variants which are explained below with the aid of the simplified flow diagrams in FIG. 1 and FIG. 2. In the interests of clarity, the reactions are in each case shown without significant amounts of isobutene in the $C_4$ feed. In the figures:

Et=ethene
$C_2^=$=ethene
$C_3^=$=propene
$C_4^=$=1- and 2-butene
$C_4$=n- and i-butane
$C_5^=$=2-pentane
$C_6^=$=3-hexene
$C_4$—Re=$C_4$ recycle
n-Bu=n-butenes
$C_2$—Re=$C_2$-recycle
$C_5$—Re=$C_5$-recycle The flow diagram shown in simplified form in FIG. 1 encompasses a reactor unit which, according to the present state of the art, preferably comprises two reactors R operated in the swing mode of synthesis/regeneration and a three-stage distillation sequence which makes it possible to discharge the $C_4$ purge stream and also pure $C_3^-$, $C_5^-$ and/or $C_6$-olefin streams.

Fresh raffinate II together with fresh ethylene and the recycle streams $C_2^=$, $C_4^-/C_4^=$ and possibly $C_5^=$ are fed into the reactor R, which is preferably operated as a fixed bed. The product stream from this, which comprises $C_2$–$C_6$-olefins and butanes, is fractionated in the distillation D1 to give a low-boiler fraction comprising ethylene and propylene which can either be fed into the work-up sequence of a cracker or is preferably fractionated in a further distillation column D3 to give the pure components ethylene and propylene and a high-boiling fraction comprising $C_4$-olefins and butanes and also 2-pentene and 3-hexene formed. Ethylene taken off at the top of D3 is at least partly recirculated to the metathesis reactor. The bottoms from column D1 are fractionated in a further column D2, which may be configured as a side-offtake column or a dividing wall column, to give a low-boiling fraction comprising $C_4$-olefins and butanes, which can be wholly or partly recirculated to the metathesis step, an intermediate-boiling fraction which preferably consists of 2-pentene and can be wholly or partly recirculated to the metathesis step, and a desired product fraction which preferably consists of 3-hexene in a high purity of at least 99%, which is preferably discharged.

A specific embodiment of the process of the present invention provides for the reactor unit R and the distillation column D1 to be linked to form a reactive distillation unit.

Figure 2:
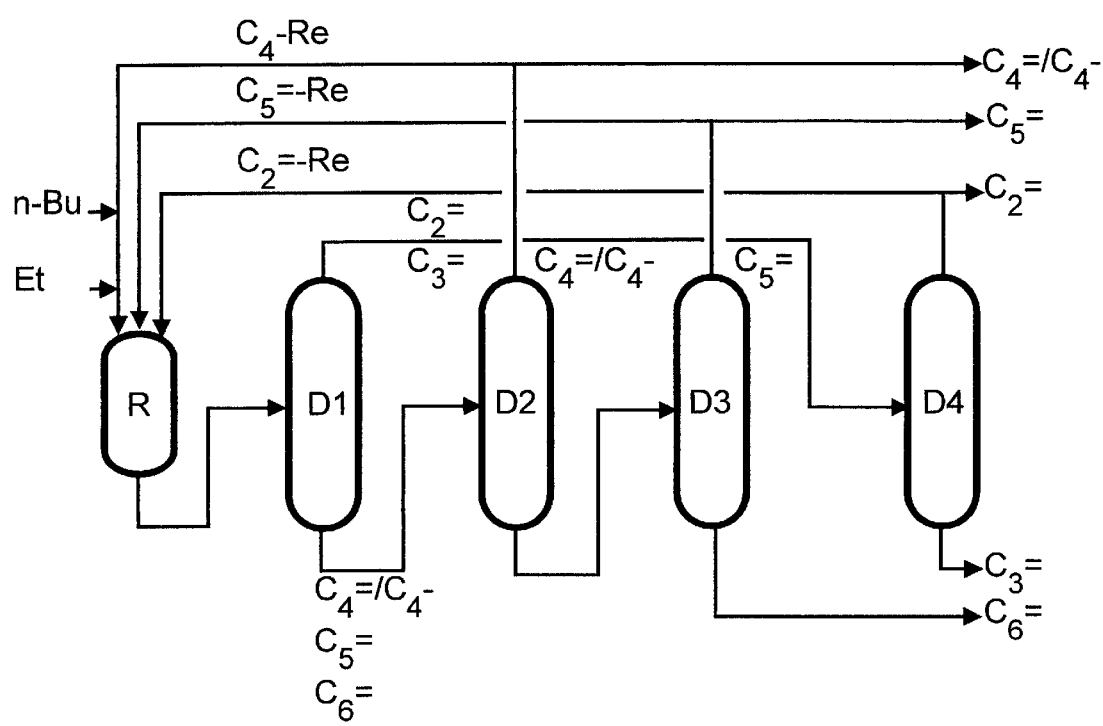

The process flow diagram shown in simplified form in FIG. 2 encompasses a reactor unit, which according to the present state of the art, preferably comprises two reactors operated in the swing mode of synthesis/regeneration, and a four-stage distillation sequence which makes it possible to discharge the $C_4$ purge stream and also pure $C_3^-$, $C_5^-$ and/or $C_6$-olefin streams.

Fresh raffinate II together with fresh ethylene and the recycle streams $C_2^=$, $C_4^-/C_4^=$ and possibly $C_5^=$ are fed into the reactor R, which is preferably operated as a fixed bed. The product stream from this, which comprises $C_2$–$C_6$-olefins and butanes, is fractionated in the distillation D1 to give a low-boiling fraction comprising ethylene and propylene, which can either be fed into the work-up sequence of a cracker or is preferably fractionated in a further distillation column D4 to give the pure components ethylene and propylene, and a high-boiling fraction comprising $C_4$-olefins and butanes and also 2-pentene and 3-hexene formed. Ethylene taken off at the top of D4 is at least partly recirculated to the metathesis reactor. The bottoms from column D1 are fractionated in a further column D2 to give a low-boiling fraction comprising $C_4$-olefins and butanes, which can be wholly or partly recirculated to the metathesis step, and a high-boiling fraction comprising 2-pentene and 3-hexene which is fractionated in the column D3 to give the pure components 2-pentene as top product, which can be wholly or at least partly recirculated to the metathesis reactor, and a $C_6$ desired product fraction comprising at least 99% of hexenes, which is discharged.

As catalysts, preference is given to heterogeneous rhenium catalysts known from the literature, for example $Re_2O_7$ on $\gamma$-$Al_2O_3$ or on mixed supports, e.g. $SiO_2/Al_2O_3$, $B_2O_3/SiO_2/Al_2O_3$ or $Fe_2O_3/Al_2O_3$, having different metal contents. The rhenium oxide content is, regardless of the support selected, in the range from 1 to 20%, preferably from 3 to 10%.

The catalysts are used in freshly calcined form and require no further activation (e.g. by means of alkylating agents). Deactivated catalyst can be regenerated a number of times by burning off carbon residues at temperatures above 400° C. in a stream of air and cooling under an inert gas atmosphere.

Comparison of heterogeneous catalysts shows that $Re_2O_7/Al_2O_3$ is active even under very mild reaction conditions (T=20–80° C.), while $MO_3/SiO_2$ (M=Mo, W) becomes active only at temperatures above 100–150° C. and consequently C=C-double bond isomerization can occur as secondary reaction.

Mention may also be made of:

$WO_3/SiO_2$, prepared from $(C_5H_5)W(CO)_3Cl$ and $SiO_2$ in J. Mol Catal. 1995, 95, 75–83;

3-component system consisting of $[Mo(NO)_2(OR)_2]n$, $SnET_4$ and $AlCl_3$ in J. Mol. Catal. 1991, 64, 171–178 and J. Mol. Catal 1989, 57, 207–220;

Nitridomolybdenum(VI) complexes from highly active precatalysts in J. Organomet. Chem. 1982, 229, $C_{19}$–$C_{23}$;

heterogeneous $SiO_2$-supported $MoO_3$ and $WO_3$ catalysts in J. Chem Soc., Faraday Trans./1982, 78, 2583–2592;

supported Mo catalysts in J. Chem. Soc., Faraday Trans./ 1981, 77, 1763–1777;

active tungsten catalyst precursor in J. Am. Chem. Soc. 1980, 102(21), 6572–6574;

acetonitrile(pentacarbonyl)tungsten in J. Catal. 1975, 38, 482–484;

trichloro(nitrosyl)molybdenum(II) as catalyst precursor in Z. Chem. 1974, 14, 284–285;

$W(CO)_5PPH_3/EtAlCl_2$ in J. Catal. 1974, 34, 196–202;

$WCl_6$/n-BuLi in J. Catal 1973, 28, 300–303;

$WCl_6$/n-BuLi in J. Catal 1972, 26, 455–458;

FR 2 726 563: $O_3ReO[Al(OR)(L)xO]nReO_3$ where R=$C_1$–$C_{40}$-hydrocarbon, n=1–10, x=0 or 1 and L=solvent, EP-A-191 0 675, EP-A-129 0 474, BE 899897: catalyst systems comprising tungsten, 2-substituted phenoxide groups and four other ligands, including a halogen, alkyl or carbene group, FR 2 499 083: catalyst system comprising a tungsten, molybdenum or rhenium oxo transition metal complex with a Lewis acid;

U.S. Pat. No. 4,060,468: catalyst system comprising a tungsten salt, an oxygen-containing aromatic compound, e.g. 2,6-dichlorophenol, and, if desired, molecular oxygen;

BE 776,564: catalyst system comprising a transition metal salt, an organometallic compound and an amine.

To improve the cycle time of the catalysts used, especially the supported catalysts, it is advisable to purify the feed over adsorber beds (guard beds). The guard bed serves to dry the $C_4$ stream and to remove substances which could act as catalyst poisons in the subsequent metathesis steps. Preferred adsorbent materials are Selexsorb CD and CDO and also 3 Å and NaX molecular sieves (13x). The purification is carried out in drying towers at temperatures and pressures which are preferably chosen so that all components are present in the liquid phase. If desired, the purification step is used to preheat the feed for the subsequent metathesis step. It may be advantageous to combine a plurality of purification steps or to connect them in series.

Pressure and temperature in the metathesis step are chosen so that all reactants are present in the liquid phase (usually from 0 to 150° C., preferably from 20 to 80° C.; p=2 to 200 bar). As an alternative, it can be advantageous, particularly in the case of feed streams having a relatively high isobutene content, to carry out the reaction in the gas phase and/or to use a catalyst which has a lower acidity.

The reaction is generally complete after from 1 s to 1 h, preferably after from 30 s to 30 min. It can be carried out continuously or batchwise in reactors such as pressurized gas vessels, flow tubes or reactive distillation apparatuses, with preference being given to flow tubes.

EXAMPLES

Example 1
Continuous Experiment on Two-Stage Selective Hydrogenation of Crude $C_4$ Fraction 1$^{st}$ Stage Crude $C_4$ fraction having a composition of 43.7% of butadiene (including butenyne and butyne), 14.3% of 1-butene, 7.8% of 2-butenes and 7.2% of n-butane is reacted with 175 standard 1 h of hydrogen over a 0.3% $Pd/Al_2O_3$ heterogeneous catalyst in a continuously operated tube reactor at a fresh feed flow of 1 kg/h of crude $C_4$ fraction and a circulation of 8.2 kg/h, an LHSV of 9.0 h$^{-1}$ and a reactor inlet temperature of 20° C. At a butadiene conversion of 95.2%, a total butene selectivity of 99.6% and a 1-butene selectivity of 56.5% were achieved in the first stage of the selective hydrogenation under these conditions.

2$^{nd}$ Stage

A typical reaction product from the first stage of the selective hydrogenation, comprising 0.53% of butadiene (including butenyne and butyne), 27.09% of 1-butene, 14.6% of 2-butenes and 11.0% of n-butane is reacted with 20 standard l/h or 10 standard l/h of hydrogen over a 0.3% $Pd/Al_2O_3$ heterogeneous catalyst (H0-13L) in a continuously operated tube reactor at a fresh feed flow of 1.7 kg/h of reaction product from the first stage and a circulation of 3.0 kg/h, an LHSV of 15 and a reactor inlet temperature of 60° C. and a reactor outlet temperature of 70° C. or 67° C. At a butadiene conversion of 99.8% or 98.5%, these conditions gave a raffinate I stream having a residual butadiene content of 10 ppm or 8 ppm at an n-butane formation of 2.7% or 1.3% and an isomer ratio of 2-butene to 1-butene of 3.4 or 1.5.

Example 2
Continuous Experiment on Separation of Isobutene by Etherification with Isobutanol In a three-stage reactor cascade, raffinate I and isobutanol are passed from the top downward through a flooded fixed bed of an acid ion exchanger, with the ratio of isobutanol to isobutene in the feed being set to 1.2. The reactor inlet temperature is 40° C., the reactor outlet temperature is 65° C. and the reaction pressure is 8 bar. The measured isobutene conversion after the first stage is 85%. In the second, similarly dimensioned reactor, the conversion is increased to 95% at a reactor inlet temperature of 40° C., a rector outlet temperature of 50° C. and a reaction pressure of 8 bar. In the third, significantly larger reactor, the equilibrium conversion is established at a reactor inlet temperature and reactor outlet temperature of 40° C. in each case and a reaction pressure of 8 bar. The raffinate stream remaining under these conditions after removal of isobutyl tert-butyl ether by distillation has a residual isobutene content of 0.7%.

Example 3
a) Continuous Experiment on Single-Stage Metathesis of Raffinate II with Addition of Ethylene and the Aim of Propylene Optimization After purification of the feed over an adsorber bed comprising molecular sieves 13x, 10.44 kg/h of a $C_4$ fraction comprising 18.9% of 1-butene, 66.1% of 2-butene and 15.0% of butanes together with 2.75 kg/h of ethylene are passed continuously at 50° C. and 30 bar in the liquid phase through a tube reactor containing heterogeneous $Re_2O_7$/$Al_2O_3$ catalyst. The reaction product is, after a residence time of 5 minutes, fractionated in a three-stage distillation sequence. A low-boiling $C_2$/$C_3$ phase is taken off at the top of the first column and is fine-distilled in a second distillation column. This gives 9.62 kg/h of PG propylene. All of the ethylene fraction obtained at the top of this column is returned to the metathesis step. The bottoms from the first column which comprise $C_4$–$C_6$-olefins and butanes, are fed to a third column where most of the low-boiling $C_4$ fraction separated off at the top is returned to the metathesis reaction. The major part of a $C_5$-olefin fraction taken off as intermediate-boiling fraction and comprising 98.5% of cis/trans-2-pentene is returned to the metathesis reactor. The high-boiling fraction of 1.38 kg/h obtained at the bottom of this column comprised 99.5% of cis/trans-3-hexene. The total butene conversion determined at a $C_4$ purge stream of 2.19 kg/h was 93.1% and the ethylene conversion was >99%.

b) Continuous Experiment on Single-Stage Metathesis of Raffinate II to Give Propylene and 3-Hexene at Reduced Ethylene Usage After purification of the feed over an adsorber bed comprising molecular sieves 13×, 10.44 kg/h of a $C_4$ fraction comprising 37.8% of 1-butene, 47.2% of 2-butene and 15.0% of butanes together with 1.38 kg/h of ethylene are passed continuously at 50° C. and 25 bar in the liquid phase through a tube reactor containing heterogeneous $Re_2O_7/Al_2O_3$ catalyst. The reaction product is, after a residence time of 5 minutes, fractionated in a three-stage distillation sequence. A low-boiling $C_2/C_3$ phase is taken off at the top of the first column and is fine-distilled in a second distillation column. This gives 6.88 kg/h of PG propylene. All of the ethylene fraction obtained at the top of this column is returned to the metathesis step. The bottoms from the first column, which comprise $C_4$–$C_6$-olefins and butanes, are fed to a third column where most of the low-boiling $C_4$ fraction separated off at the top is returned to the metathesis reaction. The major part of a $C_5$-olefin fraction taken off as intermediate-boiling fraction and comprising 98.5% of cis/trans-2-pentene is returned to the metathesis reactor. The high-boiling fraction of 2.75 kg/h obtained at the bottom of this column comprised 99.6% of cis/trans-3-hexene.

The total butene conversion determined at a $C_4$ purge stream of 2.20 kg/h was 93.0% and the ethylene conversion was >99%.

We claim:

1. A process for preparing propene and hexene from a raffinate II feed stream comprising olefinic $C_4$-hydrocarbons, which comprises
   a) a metathesis reaction in which butenes present in the feed stream are reacted with ethene in the presence of a metathesis catalyst comprising at least one compound of a metal of transition groups VIb, VIIb or VIII of the Periodic Table of the Elements to give a mixture comprising ethene, propene, butenes, 2-pentene, 3-hexene and butanes, using, based on the butenes, from 0.05 to 0.6 molar equivalents of ethene,
   b) firstly fractionally distilling the product stream obtained in this way to give a low-boiling fraction A comprising $C_2$–$C_3$-olefins and a high-boiling fraction comprising $C_4$–$C_6$-olefins and butanes,
   c) subsequently feeding into a distillation column in the work-up sequence of a cracker or fractionally distilling the low boiling fraction A obtained from b) to give an ethene-containing fraction and a propene containing fraction, with the ethene-containing fraction being returned to the process step a) and the propene-containing fraction being discharged as product,
   d) subsequently fractionally distilling the high-boiling fraction obtained from b) to give a low-boiling fraction B comprising butenes and butanes, a pentene-containing intermediate-boiling fraction C and a hexene-containing high-boiling fraction D,
   e) where the fractions B and C are completely or partly returned to the process step a) and the fraction D is discharged as product.

2. A process as claimed in claim 1, wherein step d) is carried out in a dividing wall column.

3. A process as claimed in claim 1, wherein, in step d), the high-boiling fraction obtained from b) is firstly fractionally distilled to give a low-boiling fraction B comprising butenes and butanes and a high-boiling fraction comprising 2-pentene and 3-hexene, and the high-boiling fraction is then fractionally distilled to give the fractions C and D.

4. A process as claimed in claim 1, wherein the metathesis reaction is carried out in the presence of heterogeneous metathesis catalysts which are selected from the group consisting of transition metal compounds of metals of groups VIb, VIIb and VIII of the Periodic Table of the Elements applied to inorganic supports.

5. A process as claimed in claim 4, wherein the metathesis catalyst used is rhenium oxide on γ-aluminum oxide or on $Al_2O_3/B_2O_3/SiO_2$ mixed supports.

6. A process as claimed in claim 1, wherein the raffinate II feed stream comprising olefinic $C_4$-hydrocarbons is firstly prepared by a process which comprises the substeps
   (1) removal of butadiene and acetylenic compounds, optionally by extraction of butadiene with a butadiene-selective solvent and subsequent/or selective hydrogenation of butadienes and acetylenic compounds present in crude $C_4$ fraction to give a reaction product comprising n-butenes and isobutene and essentially no butadienes and acetylenic compounds,
   (2) removal of isobutene by reaction of the reaction product obtained in the preceding step with an alcohol in the presence of an acid catalyst to form an ether, removal of the ether and the alcohol, which can be carried out simultaneously with or after the etherification, to give a reaction product comprising n-butenes and optionally oxygen-containing impurities, with the ether formed being able to be discharged or redissociated to obtain pure isobutene and the etherification step being able to be followed by a distillation step for removing isobutene, where, if desired, introduced $C_3$-, i-$C_4$- and $C_5$-hydrocarbons can also be separated off by distillation during the removal of the ether and the alcohol, and
   (3) removal of the oxygen-containing impurities from the output of substep (2) over adsorber materials.

7. A process as claimed in claim 6, wherein the substep of selective hydrogenation of butadienes and acetylenic impurities present in crude $C_4$ fraction is carried out in two stages by bringing the crude $C_4$ fraction in the liquid phase into contact with a catalyst comprising at least one metal selected from the group consisting of nickel, palladium and platinum on a support at from 20 to 200° C., a pressure of from 1 to 50 bar, an LHSV of from 0.5 to 30 $m^3$ of fresh feed per $m^3$ catalyst per hour and a ratio of recycle to fresh feed of from 0 to 30 and a molar ratio of hydrogen to diolefins of from 0.5 to 50 to give a reaction product comprising, apart from isobutene, the n-butenes 1-butene and 2-butene in a molar ratio of from 2:1 to 1:10 and containing essentially no diolefins and acetylenic compounds.

8. A process as claimed in claim 6, wherein the substep of butadiene extraction from crude $C_4$ fraction is carried out using a butadiene-selective solvent selected from the group consisting of acetone, furfural, acetonitrile, dimethylacetamide, dimethylformamide and N-methylpyrrolidone to give a reaction product in which, after subsequent selective hydrogenation/isomerization, the n-butenes 1-butene and 2-butene are present in a molar ratio of from 2:1 to 1:10.

9. A process as claimed in claim 6, wherein the substep of isobutene etherification is carried out using methanol or isobutanol in the presence of an acid ion exchanger in a three-stage reactor cascade, where the reaction mixture flows from the top downward through the flooded fixed-bed catalysts and the reactor inlet temperature is from 0 to 60° C., the outlet temperature is from 25 to 85° C., the pressure is from 2 to 50 bar, the ratio of isobutanol to isobutene is from 0.8 to 2.0 and the total conversion corresponds to the equilibrium conversion.

10. A process as claimed in claim 1, wherein the raffinate II feed stream comprising olefinic $C_4$-hydrocarbons is firstly prepared by a process which comprises the substeps (1) removal of butadiene and acetylenic compounds, optionally by extraction of butadiene with a butadiene-selective solvent and subsequent/or selective hydrogenation of butadienes and acetylenic compounds present in crude $C_4$ fraction to give a reaction product comprising n-butenes and isobutene and essentially no butadienes and acetylenic compounds, (2) removal of isobutene by oligomerization or polymerization of isobutene in the presence of a catalyst selected from the group consisting of heterogeneous catalysts comprising an oxide of a metal of transition group VIb of the Periodic Table of the Elements on an acidic inorganic support, starting from the reaction product obtained after the above-described stages of butadiene extraction and/or selective hydrogenation so as to produce a stream having a residual isobutene content of less than 15%, (3) removal of the oxygen-containing impurities from the output of substep (2) over adsorber materials.

11. A process as claimed in claim 6, wherein substep (3) is carried out using at least one guard bed comprising high surface area aluminum oxides, silica gels, aluminosilicates or molecular sieves.

* * * * *